United States Patent
Casalino et al.

(10) Patent No.: US 11,617,615 B2
(45) Date of Patent: Apr. 4, 2023

(54) APPARATUS AND COSMETIC METHOD FOR BODY ORIFICE REMODELING

(71) Applicant: BIOS SRL, Vimodrone (IT)

(72) Inventors: Aldo Casalino, Vimodrone (IT); Lorenzo Casalino, Cologno Monzese (IT)

(73) Assignee: BIOS S.r.l., Milan (IT)

( * ) Notice: Subject to any disclaimer, the term of this patent is extended or adjusted under 35 U.S.C. 154(b) by 856 days.

(21) Appl. No.: 16/539,963

(22) Filed: Aug. 13, 2019

(65) Prior Publication Data

US 2019/0365462 A1 Dec. 5, 2019

Related U.S. Application Data

(63) Continuation-in-part of application No. 15/410,044, filed on Jan. 19, 2017, now abandoned.

(51) Int. Cl.
*A61B 18/14* (2006.01)
*A61B 18/12* (2006.01)
(Continued)

(52) U.S. Cl.
CPC ...... *A61B 18/1485* (2013.01); *A61B 18/1206* (2013.01); *A61B 18/18* (2013.01);
(Continued)

(58) Field of Classification Search
CPC ............ A61B 18/1206; A61B 18/1485; A61B 18/18; A61B 2018/005; A61B 2018/00559; A61B 2018/00589; A61B 2018/00636; A61B 2018/00994; A61B 2018/1253; A61B 2018/126; A61B 2018/1405; A61B 2018/147; A61B 2018/1495; A61N 1/0524; A61N 1/06; A61N 1/36007; A61N 1/40
See application file for complete search history.

(56) References Cited

U.S. PATENT DOCUMENTS

| 4,823,614 A | 4/1989 | Drogendijk et al. |
| 5,611,768 A | 3/1997 | Tutrone, Jr. |

(Continued)

FOREIGN PATENT DOCUMENTS

| WO | 2007092610 | 8/2007 |
| WO | 2013138718 | 9/2013 |
| WO | 2015059120 | 4/2015 |

OTHER PUBLICATIONS

European Search Report—corresponding EP Application No. 20190165, dated Dec. 8, 2020, 7 pages.
(Continued)

*Primary Examiner* — Khadijeh A Vahdat
(74) *Attorney, Agent, or Firm* — ISUS Intellectual Property PLLC; Anthony Jason Mirabito

(57) ABSTRACT

A body orifice remodeling device includes a cylindrical handpiece having a defined length which is adapted to be inserted into the body orifice and an elongated monopolar electrode mounted outside on the circumference of the cylindrical handpiece and extending substantially along the length of the handpiece. A source of radio frequency (RF) energy in the handpiece is configured to generate RF energy to the elongated monopolar electrode; and a source of electromagnetic stimulation energy (EMagS) in the handpiece is configured to generate (EMagS) energy.

30 Claims, 17 Drawing Sheets

(51) Int. Cl.
*A61B 18/18* (2006.01)
*A61N 1/06* (2006.01)
*A61B 18/00* (2006.01)

(52) U.S. Cl.
CPC ............... *A61B 2018/00559* (2013.01); *A61B 2018/00636* (2013.01); *A61B 2018/126* (2013.01); *A61B 2018/1253* (2013.01); *A61B 2018/1405* (2013.01); *A61B 2018/147* (2013.01); *A61N 1/06* (2013.01)

(56) References Cited

U.S. PATENT DOCUMENTS

| | | |
|---|---|---|
| 5,771,899 A | 6/1998 | Martelly et al. |
| 5,894,842 A | 4/1999 | Rabin et al. |
| 6,022,346 A | 2/2000 | Panescu |
| 6,158,435 A | 12/2000 | Dorsey |
| 6,189,535 B1 | 2/2001 | Enhoming |
| 6,553,266 B1 | 4/2003 | Yuang |
| 2010/0296977 A1 | 11/2010 | Hancock |
| 2013/0019374 A1* | 1/2013 | Schwartz ............... A61F 13/041 428/492 |
| 2013/0245728 A1 | 9/2013 | Galen |
| 2015/0297908 A1 | 10/2015 | Ainsod et al. |
| 2015/0366747 A1 | 12/2015 | Lei |
| 2016/0121112 A1 | 5/2016 | Azar |
| 2017/0209707 A1 | 7/2017 | Casalino et al. |
| 2018/0021080 A1 | 1/2018 | Fumi |
| 2018/0333211 A1 | 11/2018 | Tomasetti et al. |

OTHER PUBLICATIONS

Italian Search Report for corresponding Italian Patent Application No. 102016000006242 dated Sep. 22, 2016, 7 pages.

* cited by examiner

APPARATUS AND COSMETIC METHOD FOR BODY ORIFICE REMODELING

RELATED APPLICATIONS

This application is related to, claims priority to and is a continuation in part (CIP) of U.S. patent application Ser. No. 15/410,044, filed Jan. 19, 2017, (hereinafter "the incorporated application"), the entire contents of which are incorporated by reference herein.

FIELD OF THE INVENTION

The present invention relates to body orifice remodeling using energy devices, mainly radio frequency (RF) energy devices and electromagnetic stimulation (EMagS) energy devices and methods of cosmetically applying such devices to body orifices, including the vagina and the anus.

BACKGROUND OF THE PRESENT INVENTION

It is a known phenomenon that, as people age, the muscles in their bodily orifices, but particularly the vagina and the anus, become stretched and lose their tightness. Devices are known in the art which are directed to attempting to reverse this condition and return the tissue to a tighter state of repose.

Some of these devices use RF energy, while others implement heat energy, ultrasound, electrical energy and/or light energy. However, as these particular areas are sensitive, it is desirable that these devices treat the patient but not cause damage to the tissue, pain or discomfort.

Many of these devices are handheld devices in that the doctor or other operator must hold and manipulate the device during the entire treatment process. This can cause fatigue for the doctor or operator. If the device is left in the orifice without holding it in position, it can be pushed out of the orifice wholly or partially such that treatment is impaired or even rendered ineffective.

Another issue with such known devices is the potential appearance of "hot spots" in which one portion of the tissue in the orifice may be overtreated while other portions may be undertreated or even untreated.

Generally, such devices may rely on a single type of energy source rather than combining a number of energy sources that may provide a synergistic treatment regime.

It is also known in the art to treat patients with some form of electromagnetic stimulation (EMagS), particularly treatments designed to treat the vagina, areas around the vagina, or the pelvic or anus muscles. These usually involve some form of chair or platform that the patient sits on and the energy is provided to the general areas described above. One problem with this arrangement is that the whole areas is treated, which may be unnecessary or even ineffective since there with the specific tissue sought to be treated and the source of the energy applied. Because such emitters, usually incorporated in chairs, are necessarily very far distant from the pelvic muscles, with great loss of energy (the loss of energy with respect to the distance of the muscles to be contracted), too obtain satisfactory results a very high magnetic field intensity is required, and this can cause undesirable contractions of other muscles. EMagS is also known as magnetic nerve muscle stimulation and usually employs a pulsed electromagnetic field that employs electromagnetic stimulation using time-varying and high-power magnetic field based on a high value of magnetic flux density and/or high repetition rate.

In the case of the present invention, being very close to the pelvic muscles, a much less intense magnetic field is sufficient, which due to its proximity will be extremely directional.

An example of another known EMagS device is described in US2016/317827, but the device described operates the RF device at high frequencies, such as 13.56 Mhz, 27.12 Mhz or 40.68 Mhz, or 2.45 Ghz, frequencies much higher that those of the present invention (up to 6 Mhz).

The present application remediates this problem by incorporating a source of it is to the improvement of the foregoing shortcoming that the present application is directed.

SUMMARY OF THE PRESENT INVENTION

In an aspect, a body orifice remodeling device includes: a cylindrical handpiece having a defined length which is adapted to be inserted into the body orifice; an elongated monopolar electrode mounted outside on the circumference of the cylindrical handpiece and extending substantially along the length of the handpiece; the monopolar electrode may be of a shape conforming to the cylindrical shaped handpiece; the monopolar electrode may be a capacitive electrode, the electrode further being insulated with biocompatible material; a source of radio frequency (RF) energy may be provided in the handpiece which is configured to generate RF energy to the elongated monopolar electrode; a source of electromagnetic stimulation energy (EMagS) may be provided in the handpiece and is configured to generate (EMagS) energy; further, a controller may be provided which is configured to: (1) cause the source of RF to generate RF energy; (2) cause the source of EMagS energy to generate EMagS energy within the body orifice; and, (3) regulate the application of RF energy and EMagS energy. In the device, the body orifice may be a vagina.

In another aspect, the controller may be configured to cause the source of RF energy and the source of EMagS energy to be activated one of: simultaneously or sequentially. The controller may be configured to cause the source of RF energy and the source of EMagS energy to be activated simultaneously.

In a further aspect, the device handpiece comprises two sections: a distal section adapted to be inserted into the vagina and a proximal section, the distal section and the proximal section being separable. The distal section is of: a disposable material or a sterilizable material. The proximal section may comprise one or more connections to one or more sources of power to power the source of RF energy and the source of EMagS energy. The distal section may comprise one or more RF electrodes. The one or more electrodes may be embedded in a thermo gel to, when activated, minimize hot spots.

In yet another aspect, the device may further include a garment to retain the handpiece in position in the vagina without the need to hold the handpiece in place during treatment.

In another aspect, the distal section of the handpiece may be curved to match the contours of the human vagina. Further, the interior of the handpiece may be substantially hollow and further comprising a plurality of apertures from the interior of the handpiece through to the outside of the handpiece, further comprising a substance contained within or insertable into the interior of the handpiece which may be pumped from the interior to the exterior of the handpiece during treatment. The substance may include HA. The garment may be in the form of short pants or may be in the form of a belt. The RF energy may be applied preferable at frequencies up to 6 Mhz.

In an aspect, a method of remodeling a body orifice comprises: providing a cylindrical handpiece having a defined length which is adapted to be inserted into the body orifice; providing an elongated monopolar electrode mounted outside on the circumference of the cylindrical handpiece and extending substantially along the length of the handpiece, the monopolar electrode being of a shape conforming to the cylindrical shaped handpiece, the monopolar electrode being a capacitive electrode, the electrode further being insulated with biocompatible material; providing a source of radio frequency (RF) energy in the handpiece which is configured to generate RF energy to the elongated monopolar electrode; further providing a source of electromagnetic stimulation energy (EMagS) in the handpiece which is configured to generate (EMagS) energy; providing a controller, and wherein, in the method, the controller: (1) causes the source of RF to generate RF energy; (2) causes the source of EMagS energy to generate EMagS energy within the body orifice; and, (3) regulates the application of RF energy and EMagS energy. The body orifice may be a vagina.

In another aspect, the controller causes the source of RF energy and the source of EMagS energy to be activated one of: simultaneously or sequentially. The handpiece comprises two sections: a distal section adapted to be inserted into the vagina and a proximal section, the distal section and the proximal section being separable, wherein the distal section is of: a disposable material or a sterilizable material.

DETAILED DESCRIPTION OF THE PRESENT INVENTION

As described in the incorporated application, the present invention is directed to a device and method for remodeling body orifices. While the discussion in this specification is directed to vaginal laxity treatments, it is to be understood that the present invention and the specification is applicable to other body orifices, such as the anus.

A number of devices is illustrated and described in the incorporated application. These devices shown in FIGS. 1 through 7 employ a device in an elongated shape with a curved or round cross section having a diameter designed to be easily inserted into the body orifice. It is envisioned that these devices, termed "probes" throughout this disclosure may be of different lengths and cross-sectional diameters to suit the particular orifice or particular body. An example of a suitable monopolar generally cylindrical probe is illustrated in FIG. 2.

Figure 2:
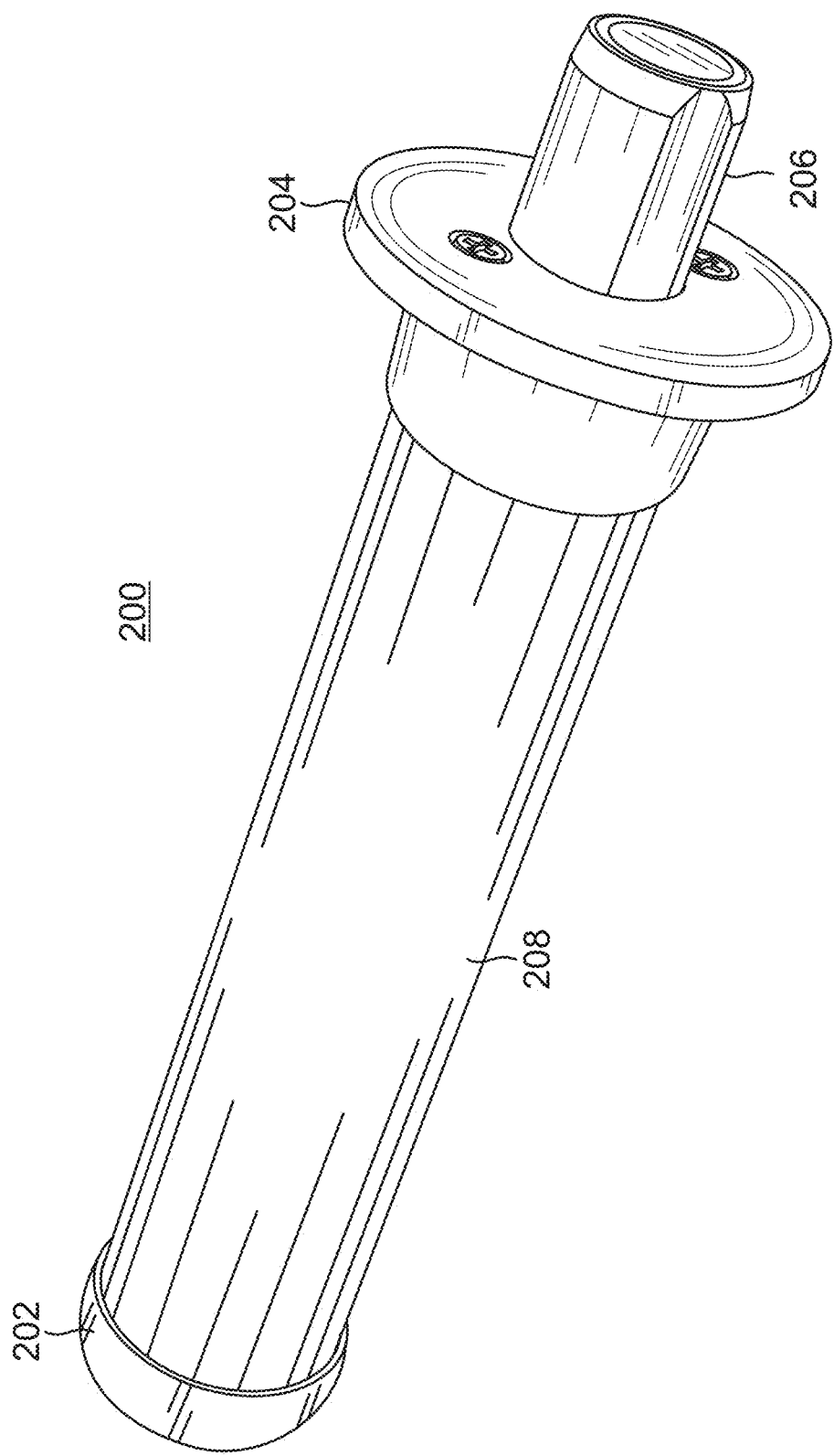
FIG. 2 illustrates another embodiment of a device in accordance with the present invention.

In FIG. 2, a probe 200 is in a generally cylindrical form, and may be of a length and width suited for the particular orifice into which it may be inserted as well as the particular person within whom the device will be inserted. Thus, the device 200 may in fact be a set of devices of various lengths and widths.

Figure 6A:
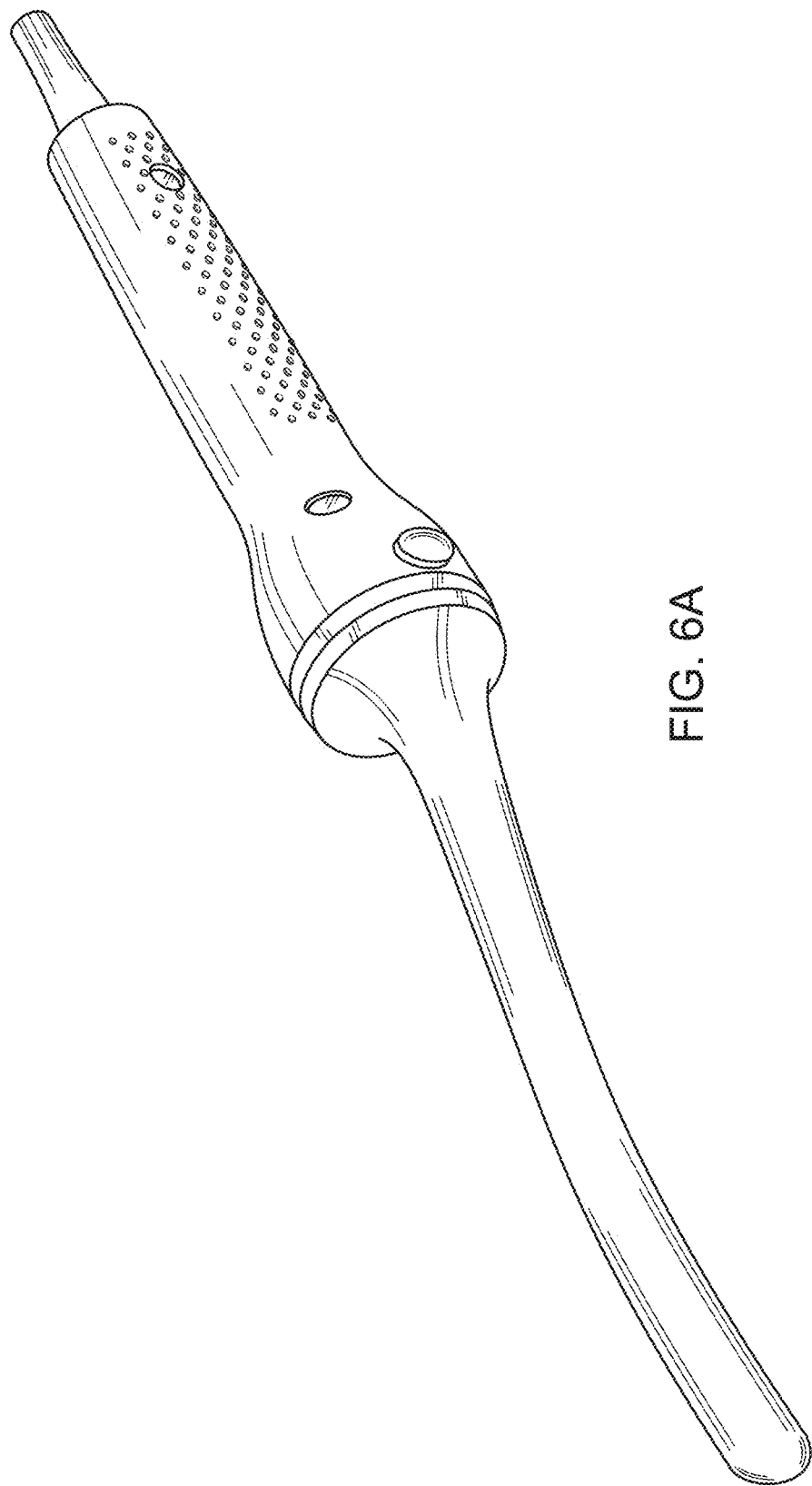
FIGS. 6A-6P illustrate designs for the device of FIG. 1.
Figure 6B:
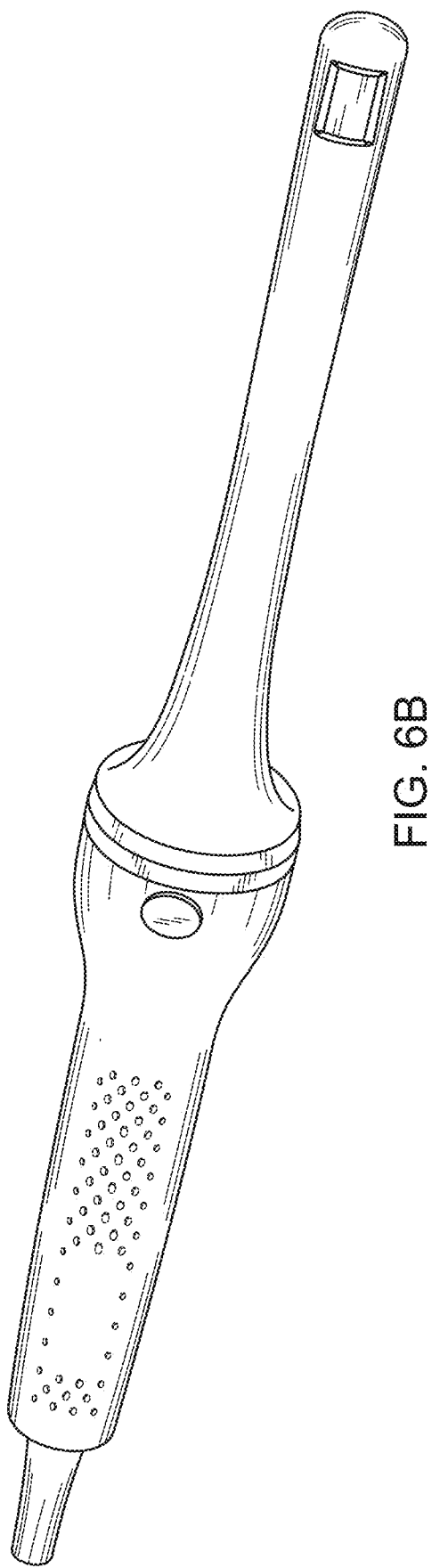
Figure 6C:
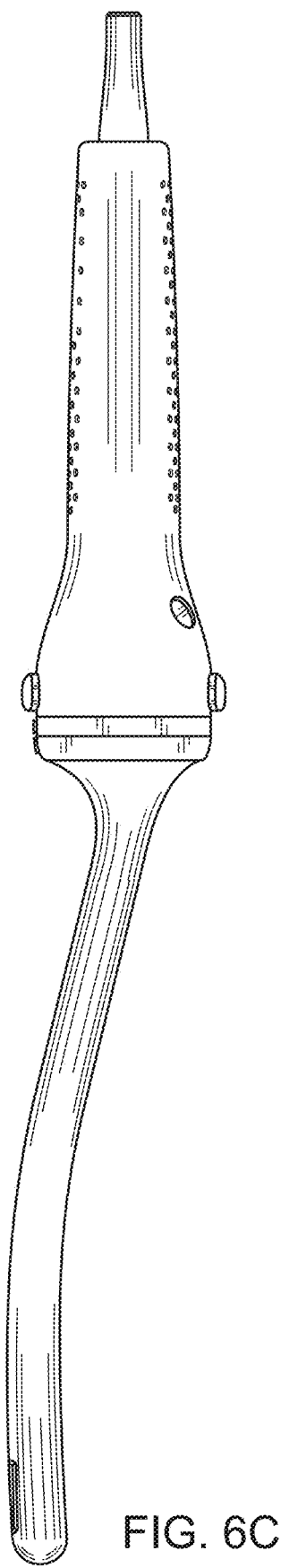
Figure 6D:
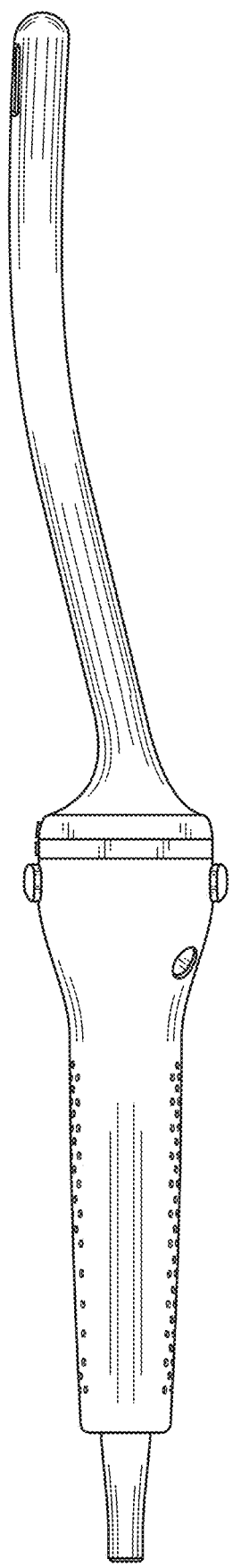
Figure 6E:
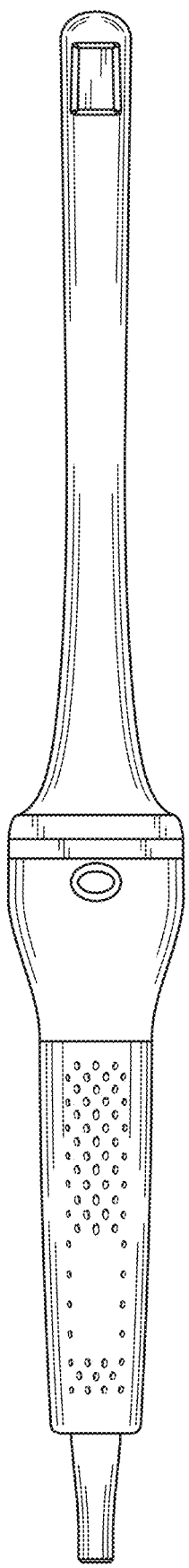
Figure 6F:
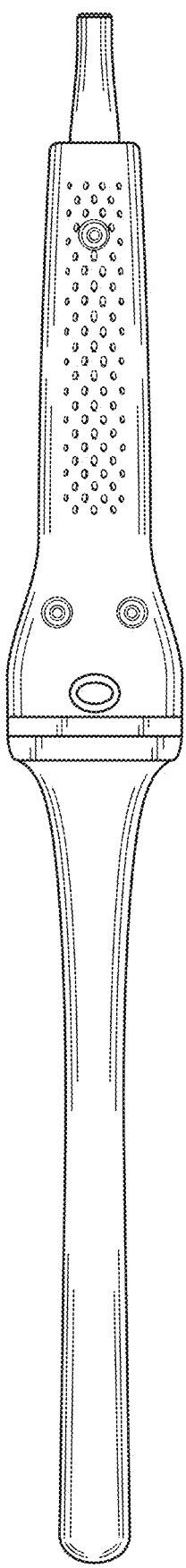
Figure 6G:
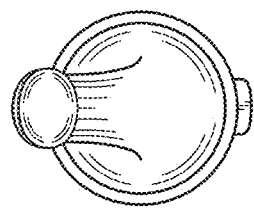
Figure 6H:
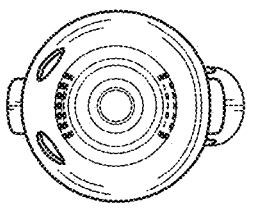
Figure 61:
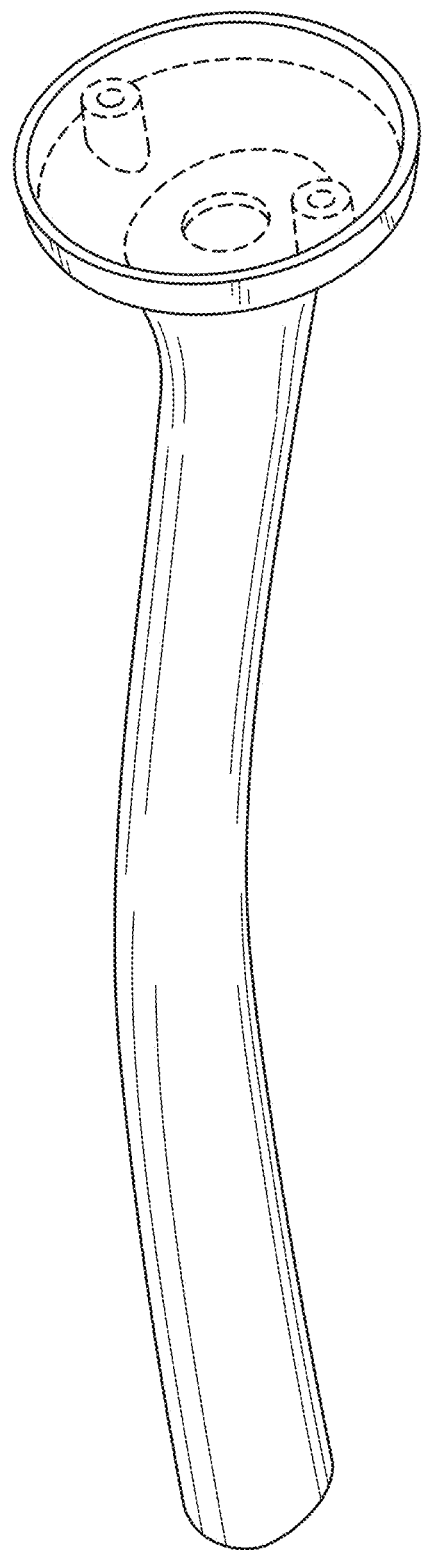
Figure 6J:
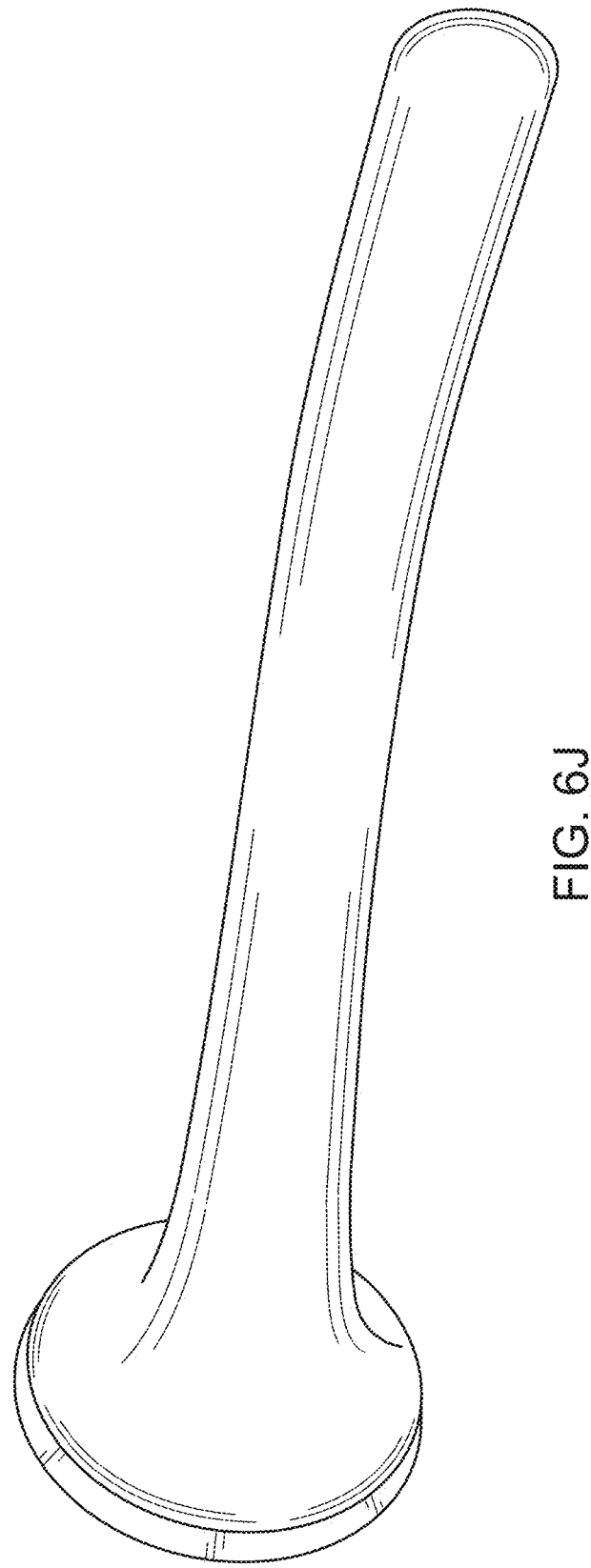
Figure 6K:
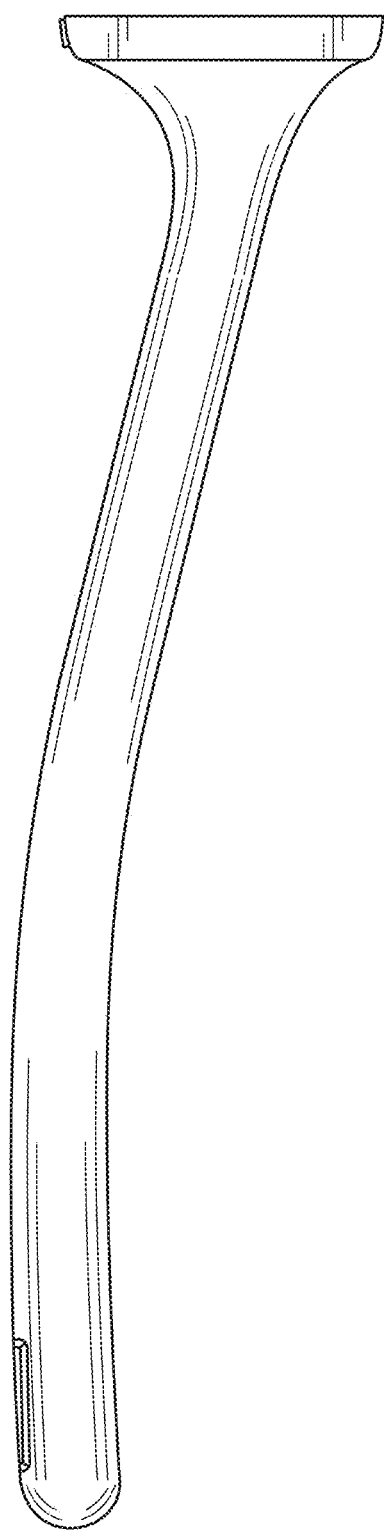
Figure 6L:
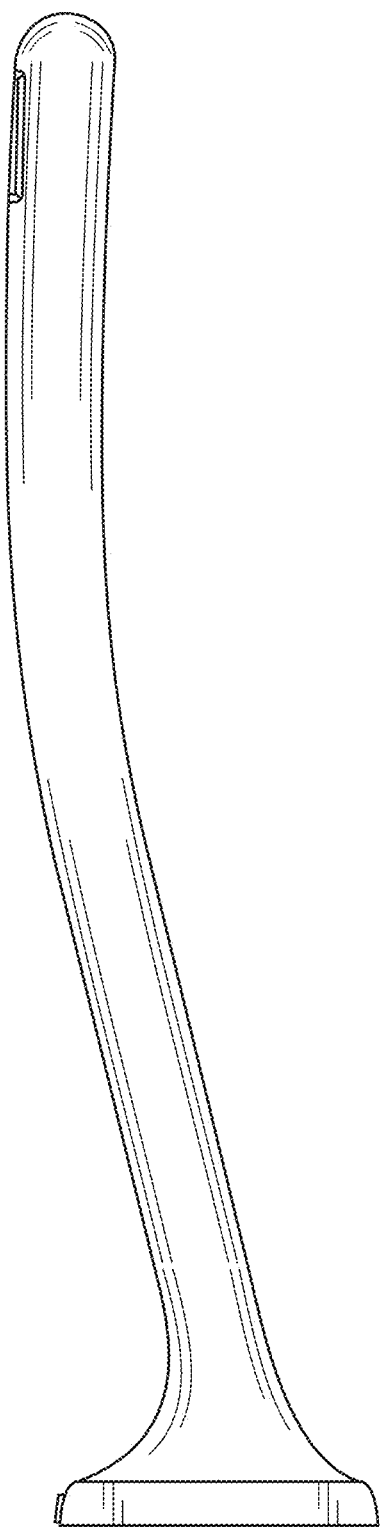
Figure 6M:
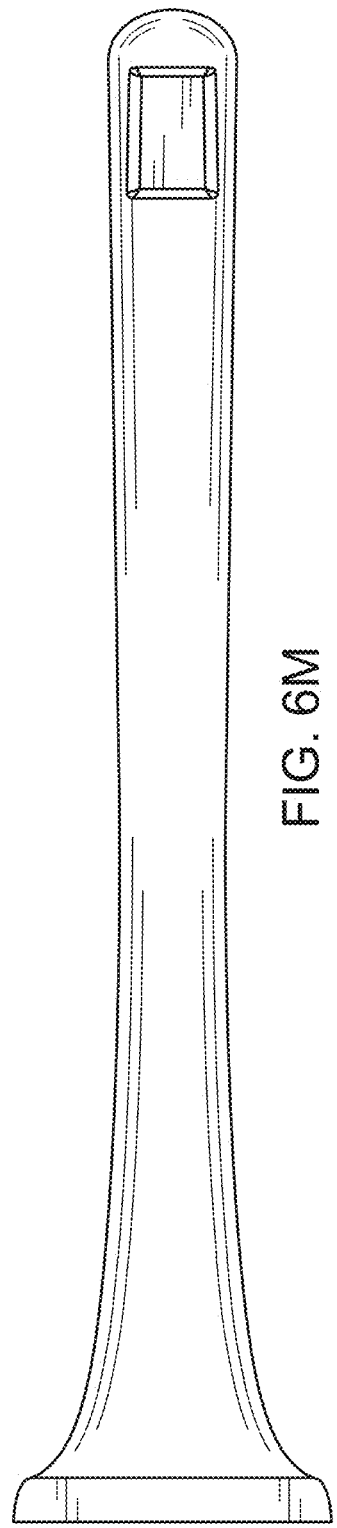
Figure 6N:
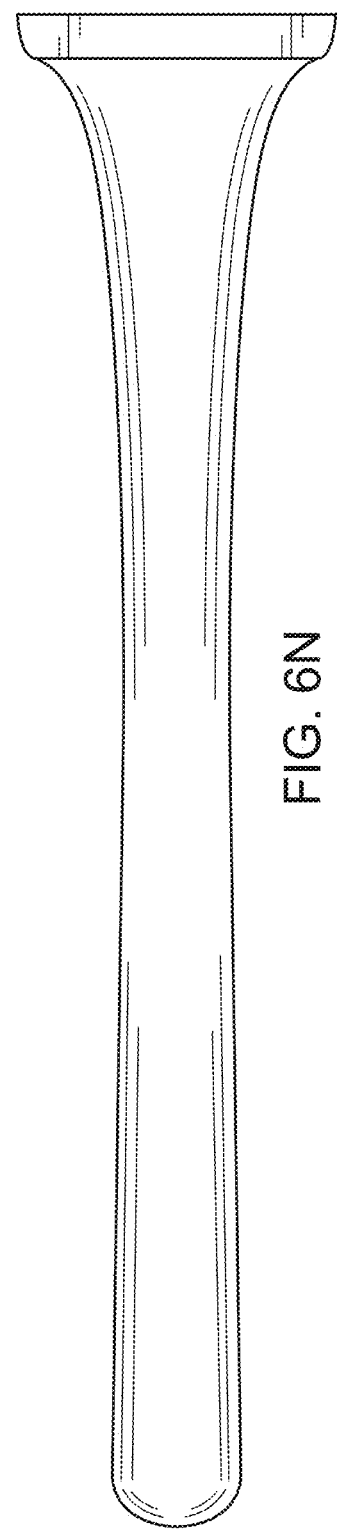
Figure 6O:
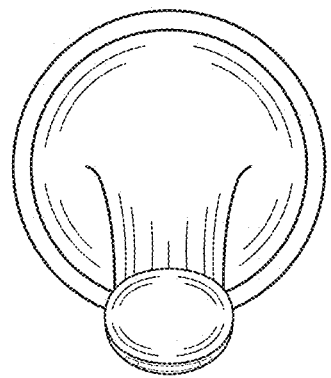
Figure 6P:
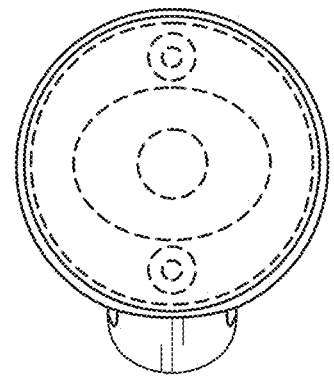

FIGS. 6A through 6P illustrate another embodiment of a probe, in this embodiment a probe which is anatomically designed to fit into a human vagina. A RF electrode may be fitted into the distal portion of the probe. As well, the distal portion of the probe may be detachable from the proximal portion of the probe. The distal portion of the probe may be a disposable element or a sterilizable element, and separating the distal portion from the proximal portion facilitates replacement or sterilizing the distal portion. The proximal portion of the probe may include electrical connections to a source of electrical power that mate with electrical connections in the distal portion of the probe that can activate and operate any RF and/or EMagS devices or other devices (such as EMS devices) contained in the distal portion of the probe.

The probe 200 includes a distal end portion 202 and a proximal end portion 204, the distal end port preferably being rounded or at least having a smooth surface to facilitate insertion into the body orifice. The proximal end port 204 may include a connector electrode 206 to facilitate an electrical connection from the outside of the probe to the inner workings within the probe, to be discussed herein. The outside of the cylindrical portion 208 may contain any number of RF electrodes, but shown here is a single monopolar electrode that may extend substantially along the entire cylindrical portion 208. The purpose of this arrangement is so that the entire body cavity may be treated without having to move the probe during treatment.

The monopolar RF electrode may be connected to a source of electrical power and a controller that interfaces the power to the one (or more) RF electrode(s). The RF electrodes may be in many forms: Monopolar, bipolar and multipolar, all of which are generally known electrodes used in patient treatment applications, such as facial treatments to reduce wrinkles and facial lines. The RF electrode preferably operates at frequencies up to 6 Mhz.

The probe may be solid in form, or, as described in the incorporated application, partially or fully hollow. The one or more RF electrodes may be mounted either on the outside of the probe or mounted within the probe, as desired and as described.

Given that a probe of the type contemplated may be inserted in some very sensitive portions of the body and given that the treatment using RF energy generates heat, it may be important to insure that there are no "hot spots" such that one portion of the probe generates more (or less) heat than another ion.

The present invention resolves the problem by incorporating a thermal gel substance, such as KERATHERM® Thermal Greases available from www.kerafol.com, within a hollow port of the probe if so constructed or in a housing with an RF electrode, depending on whether the RF electrode or electrodes are mounted within the probe or on the outside surface of the probe. When electrical power is supplied to the one or more RF electrodes, the thermal gel will act to "homogenize" the heat output so that hot spots are eliminated or at least substantially minimized.

As mentioned, presently the doctor or other operator will hold the probe in his or her hand while the treatment is being performed. If not held, it has been found that the probe may slip out or be pushed out of the orifice, with the consequent loss or reduction in treatment efficiency. The present invention eliminates this problem by incorporating an apparatus that holds the probe in place. This may be something as simple as a belt which incorporates the probe and hold sit within the body orifice or even "short pants" 300 that incorporate the probe and hold it in place, such as may be seen in FIG. 3. In this arrangement, the probe may be insertable into an aperture 302 in the "pants" located in the vicinity of the orifice being treated, or the probe may even come assembled on the pants in a more or less permanent fashion.

It is known in the art to treat patients with some form of electromagnetic stimulation (EMagS) emitter, particularly treatments designed to treat the vagina, areas around the vagina, or the pelvic or anus muscles. These known devices usually involve some form of chair or platform that the patient sits on and the energy is then provided to the general areas described above. One problem with this arrangement is that the whole area is treated, which may be unnecessary or even ineffective in treating the specific tissue sought to be treated. Because such emitters, usually incorporated in chairs, are necessarily very far distant from the pelvic muscles, with great loss of energy (the loss of energy with respect to the distance of the muscles to be contracted). To obtain satisfactory results, a very high magnetic field intensity is required, and this can cause undesirable contractions of other muscles.

In the present invention, with the probe being very close to the pelvic muscles, a much less intense magnetic field is sufficient, which due to its proximity will be extremely directional.

The present application remediates the problems outlines above by incorporating a source of EMagS energy within or on the probe. In this manner, the EMagS may be applied directly to the tissue sought to be treated. The EMagS energy may be applied in combination with the RF energy, one or before, after or during treatment using the RF electrodes, but preferably simultaneously.

Figure 4:
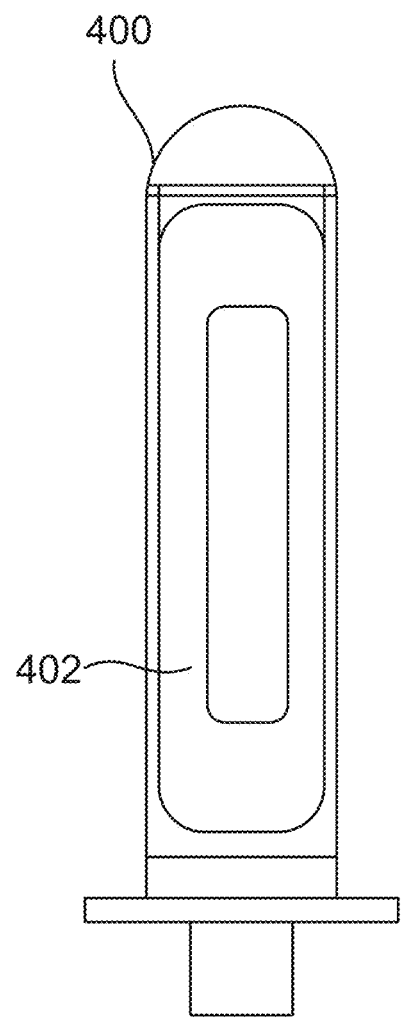
FIG. 4 illustrates an electromagnetic generating device which may be incorporated within the device of FIG. 2

Turning now to FIG. 4, this figure shows the interior portion of the probe 400 and is shown as containing a loop device 402 which, when supplied with electrical power from outside of the probe, generates electromagnetic energy to directly treat the body portions intended.

Further, as described in U.S. patent application Ser. No. 14/970,585, filed Dec. 16, 2015, entitled "APPARATUS AND METHOD FOR COSMETIC TREATMENT OF HUMAN MUCOSAL TISSUE", and assigned to the common corporate parent entity as the present invention, an electrical muscle stimulation (EMS) device may additionally be combined with a RF treatment device for treating, for example, the vagina, in that the EMS is applied to draw the tissue to contact with the probe such that the RF energy treatment becomes more effective. In fact, all three modalities: RF, EMagS, and EMS may be incorporated in the probe for treatments.

Figure 5:
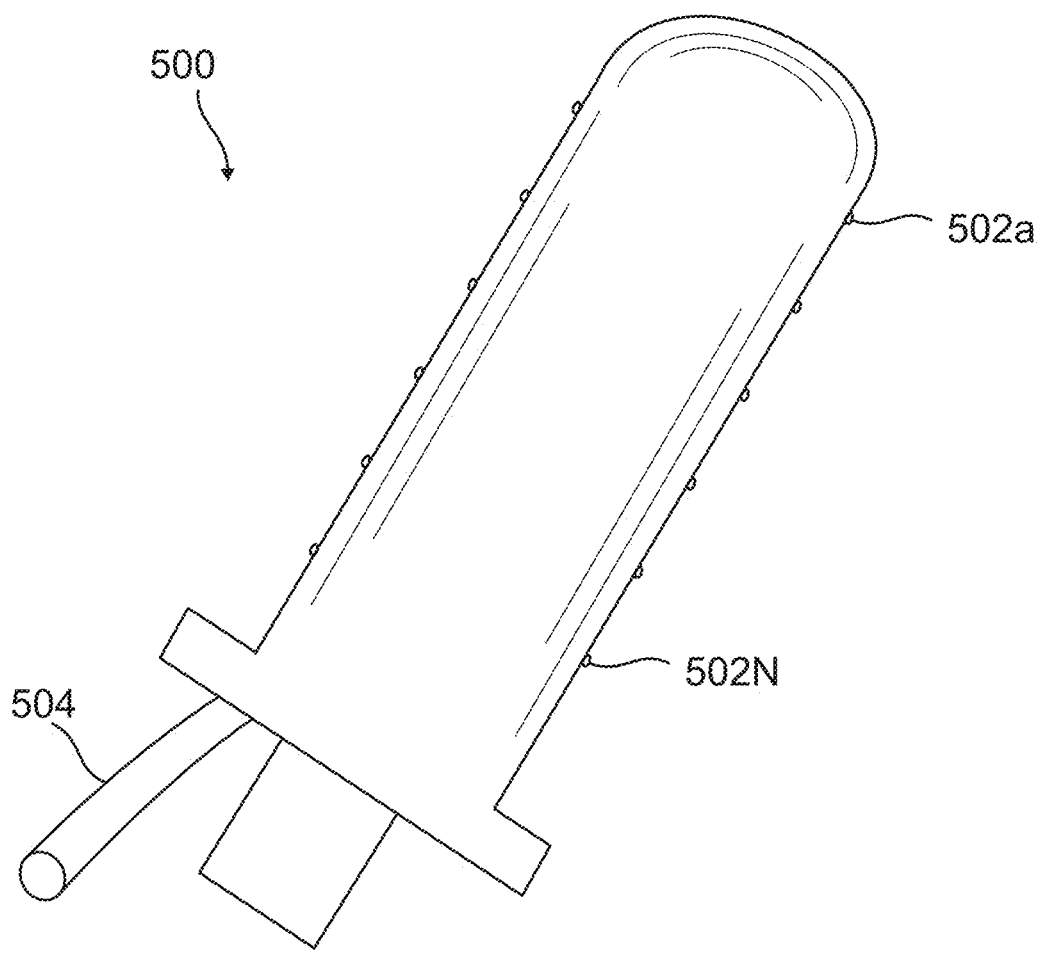
FIG. 5 illustrates a hollow device into which a fluid may be introduced.

In addition, it may be desirable to inject medicines or other materials into the orifice either before, during or after application of any one or more of RF, EMagS or EMS treatments. This may be accomplished by utilizing the hollow or at least partially hollow portion of the probe to store such material, to add apertures that pass through from the hollow portion to and through the probe outer surface, as may be seen in reference to FIG. 5. As shown in FIG. 5, the probe 500 may include a plurality of apertures 502*a*-502*n* through which the materials may be ejected from within the interior of the probe or through a conduit 504 from outside of the probe to the inside of the probe and then out of the apertures 502*a*-502*n*. The material may then at the desired time be pushed out of the interior volume of the hollow probe and through the apertures to contact and treat the tissue. This may be accomplished through a simple plunger-like device (as in a syringe) or a pressure-inducing device mounted on the end of the probe which is not inserted into the orifice.

Figure 3:
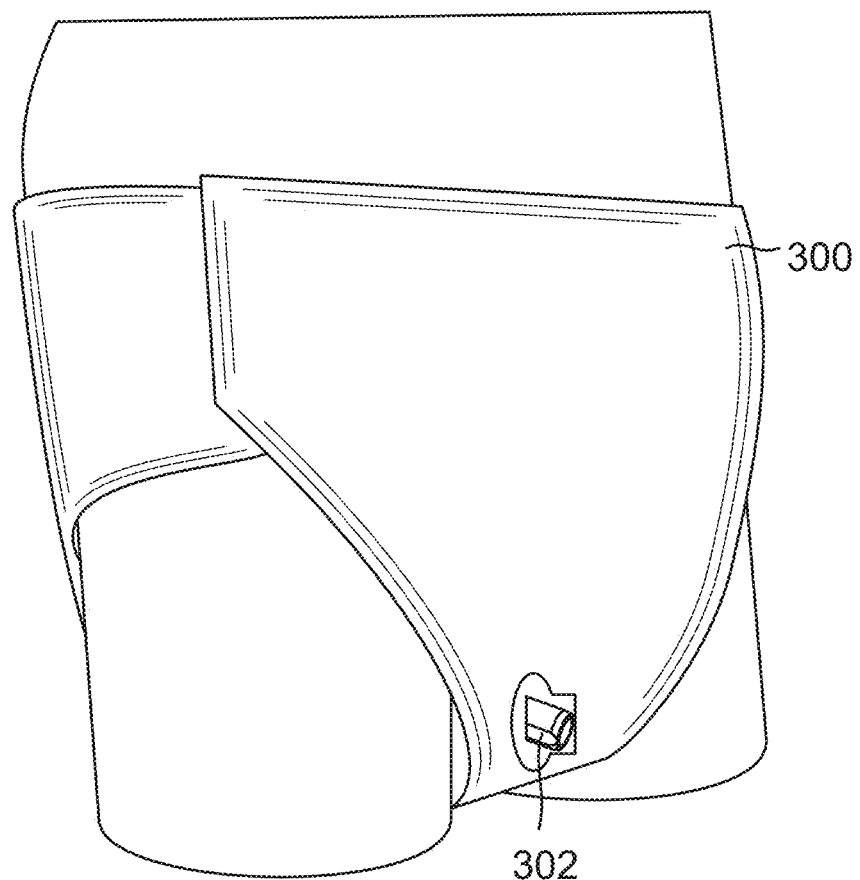
FIG. 3 illustrates an embodiment of an article of clothing that is usable with the device of FIG. 2.

While a generally cylindrical probe has been described and shown in FIG. 3, it may be desirable to provide a probe shaped to accommodate the actual interior contours of, for example, the human vagina. FIGS. 6A to 6P illustrate such a contoured probe.

Figure 1:
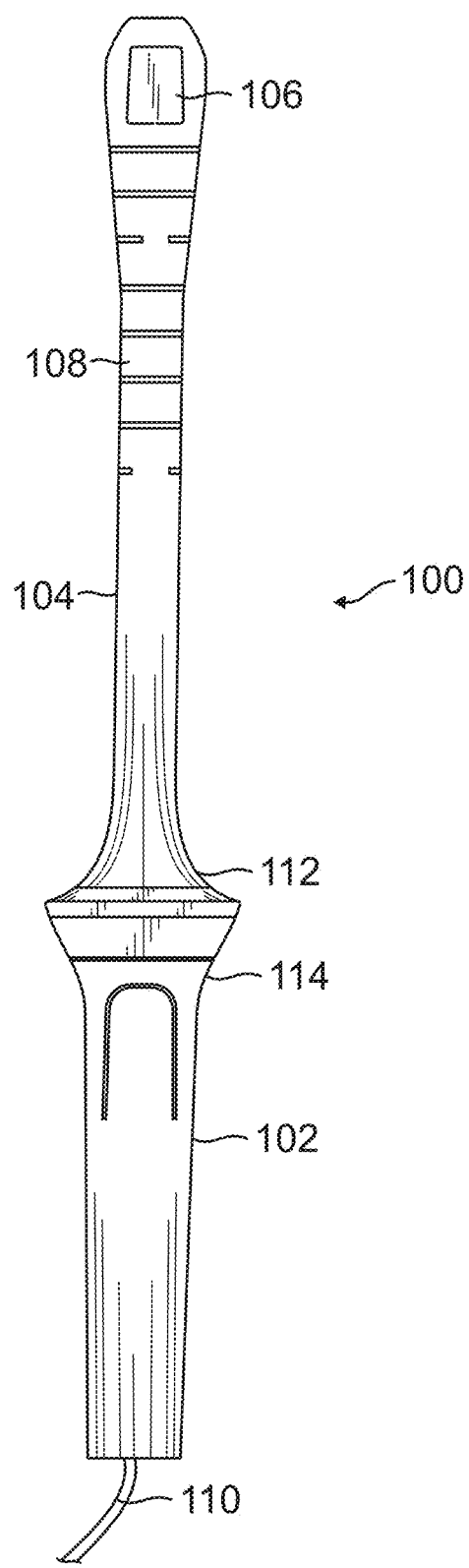
FIG. 1 illustrates one embodiment of a device in accordance with the present invention.

As shown in FIG. 1, the contoured probe 100 includes a hand hold 102 which may be gripped and manipulated by the doctor or operator. Distally of the hand hold is the operable portion 104 of the probe, which may be inserted into the body orifice. At the distal end of the probe a RF electrode 106 is shown, although, as mentioned above, more than one RF electrode may be supplied. Distance markings 108 may be included so that the distance the probe has penetrated into the orifice may be gauged.

It should be pointed out that the distance marking in FIG. 1 is only an example of marking. While in FIG. 1 the marking illustrated is in centimeters, the marking on the probe could be divided into other distance measurement units (inches) that represent the length of the electrode, so that the physician or other operator can visualize the positioning of the probe in the body orifice into which it has been inserted.

A source of electrical power is fed to the proximal end of the probe at 110. The RF electrode 106 may be encased in a casing which is filled or partially filled with thermal gel as described above. A temperature measuring device may be included either outside of the casing, or inside, or both to measure the temperature of the RF electrode. Other temperature measuring devices may be mounted on the outside surface of the probe to measure tissue temperature directly.

The probe 100 may be provided in two separable portions, portion 112 and portion 114. Unlike other of such probes that are unitary in structure and require that the entire device be disposed of or sterilized, the distal portion 112 may be of a disposable material or sterilizable material that can be reused after each patient's treatment. The portion 114 may contain electrical connections, etc. at its proximal end base portion, and may be reusable over and over again and attached to the portion 112. Further, the portion 114, which may be in the shape of a handle, may incorporate a slip ring at its base, proximal end, or a similar known structure, so that as the handle portion 114 is rotated while in position within the patient's body, the cable attached to the proximal end portion will remain stationary, so as to avoid kinking and twisting of the cable.

In addition, the portion 112 may be made in different shapes, diameters and lengths to suit the anatomy of individual patients being treated.

What we claim is:

1. A body orifice remodeling device comprising:
   a cylindrical handpiece having a defined length which is adapted to be inserted into the body orifice;
   an elongated monopolar electrode mounted outside on the circumference of the cylindrical handpiece and extending substantially along the length of the handpiece;
   the monopolar electrode of a shape conforming to the cylindrical shaped handpiece;
   the monopolar electrode being a capacitive electrode, the electrode further being insulated with biocompatible material;

a source of radio frequency (RF) energy in the handpiece which is configured to generate RF energy to the elongated monopolar electrode to treat tissue of the body orifice;

a source of electromagnetic stimulation energy (EMagS) in the handpiece which is configured to generate (EMagS) energy in the form of a pulsed and directional magnetic field to stimulate muscles and treat the tissue of the body orifice;

a controller configured to: (1) cause the source of RF to generate RF energy; (2) cause the source of EMagS energy to generate EMagS energy within the body orifice; and, (3) regulate the application of RF energy and EMagS energy.

2. The device of claim 1, wherein the body orifice is a vagina.

3. The device of claim 2, wherein the distal section of the handpiece is curved to match the contours of the human vagina.

4. The device of claim 1, wherein the controller is configured to cause the source of RF energy and the source of EMagS energy to be activated one of: simultaneously or sequentially.

5. The device of claim 1, wherein the controller is configured to cause the source of RF energy and the source of EMagS energy to be activated simultaneously.

6. The device of claim 1, wherein the handpiece comprises two sections: a distal section adapted to be inserted into the vagina and a proximal section, the distal section and the proximal section being separable.

7. The device of claim 6, wherein the distal section is of: a disposable material or a sterilizable material.

8. The device of claim 6, wherein the proximal section comprises one or more connections to one or more sources of power to power the source of RF energy and the source of EMagS energy.

9. The device of claim 1, wherein the electrode is embedded in a thermo gel to, when activated, minimize hot spots.

10. The device of claim 1, further comprising a garment to retain the handpiece in position in the vagina without the need to hold the handpiece in place during treatment.

11. The device of claim 10, wherein the garment is in the form of short pants.

12. The device of claim 10, wherein the garment is in the form of a belt.

13. The device of claim 1, wherein the interior of the handpiece is substantially hollow and further comprising a plurality of apertures from the interior of the handpiece through to the outside of the handpiece, further comprising a substance contained within or insertable into the interior of the handpiece which may be pumped from the interior to the exterior of the handpiece during treatment.

14. The device of claim 13, wherein the substance comprises HA (Hyaluronic Acid).

15. The device of claim 1, wherein the source of RF energy operates at frequencies up to 6 Mhz.

16. A method of remodeling a body orifice comprising:
providing a cylindrical handpiece having a defined length which is adapted to be inserted into the body orifice;
providing an elongated monopolar electrode mounted outside on the circumference of the cylindrical handpiece and extending substantially along the length of the handpiece, the monopolar electrode being of a shape conforming to the cylindrical shaped handpiece, the monopolar electrode being a capacitive electrode, the electrode further being insulated with biocompatible material;
providing a source of radio frequency (RF) energy in the handpiece which is configured to generate RF energy to the elongated monopolar electrode to treat tissue of the body orifice;
further providing a source of electromagnetic stimulation energy (EMagS) in the handpiece which is configured to generate (EMagS) energy in the form of a pulsed and directional magnetic field to stimulate muscles and treat the tissue of the body orifice;
providing a controller, the controller: (1) causing the source of RF to generate RF energy;
(2) causing the source of EMagS energy to generate EMagS energy within the body orifice; and, (3) regulating the application of RF energy and EMagS energy.

17. The method of claim 16, wherein the body orifice is a vagina.

18. The method of claim 17, wherein the distal section of the handpiece is curved to match the contours of the human vagina.

19. The method of claim 16, wherein the controller causes the source of RF energy and the source of EMagS energy to be activated one of: simultaneously or sequentially.

20. The method of claim 16, wherein the controller causes the source of RF energy and the source of EMagS energy to be activated simultaneously.

21. The method of claim 16, wherein the handpiece comprises two sections: a distal section adapted to be inserted into the vagina and a proximal section, the distal section and the proximal section being separable.

22. The method of claim 21, wherein the distal section is of: a disposable material or a sterilizable material.

23. The method of claim 21, wherein the proximal section comprises one or more connections to one or more sources of power to power the source of RF energy and the source of EMagS energy.

24. The method of claim 1, wherein the electrode is embedded in a thermo gel to, when activated, minimize hot spots.

25. The method of claim 16, further comprising a garment to connect to the handpiece for positioning within the body orifice, and the further step of connecting the handpiece to the garment, thus eliminating the need to hold the handpiece in place during treatment.

26. The method of claim 25, wherein the garment is in the form of short pants.

27. The method of claim 25, wherein the garment is in the form of a belt.

28. The method of claim 16, wherein the interior of the handpiece is substantially hollow and further comprising a plurality of apertures from the interior of the handpiece through to the outside of the handpiece, further comprising a substance contained within or insertable into the interior of the handpiece which may be pumped from the interior to the exterior of the handpiece during treatment.

29. The method of claim 28, wherein the substance comprises HA (Hyaluronic Acid).

30. The method of claim 16, wherein the source of RF energy operates at frequencies up to 6 Mhz.

* * * * *